United States Patent [19]

Guddal

[11] 4,098,796
[45] Jul. 4, 1978

[54] P-TRIMETHYLSILYLOXYPHENYL GLYCYLOXYPHTHALIMIDE

[75] Inventor: Erling Guddal, Skovlunde, Denmark

[73] Assignee: Novvo Industri A/S, Bagsvaerd, Denmark

[21] Appl. No.: 693,516

[22] Filed: Jun. 7, 1976

[51] Int. Cl.$^2$ .................................................. C07D 209/34
[52] U.S. Cl. ............................... 260/326 E; 260/239.1; 260/326.4; 544/26
[58] Field of Search ........................................ 260/326 E

[56] References Cited

U.S. PATENT DOCUMENTS

| | | | |
|---|---|---|---|
| 3,576,031 | 4/1971 | Holub et al. | 260/326 E X |
| 3,770,768 | 11/1973 | Holub et al. | 260/326 E |
| 3,787,439 | 1/1974 | Holub et al. | 260/326 E |

Primary Examiner—Ethel G. Love
Attorney, Agent, or Firm—Watson, Cole, Grindle & Watson

[57] ABSTRACT p-Trimethylsilyloxy-D-(—)-phenylglycyloxysuccinimide or -phthalimide, process of preparing p-trimethylsilyloxy-D-(—)-phenylglycyloxysuccinimide or -phthalimide by reacting D-(—)-p-trimethylsilyloxyphenylglycin-N-carboxyanhydride with a N-hydroxyimide, and process for preparing 6-(p-hydroxyphenylglycylamido)-penam or 7-(p-hydroxyphenylglycylamido)-cephem compounds by reacting p-trimethylsilyloxy-D-(—)-phenylglycyloxysuccinimide or -phthalimide with a phosphite amide of an ester of 6-aminopenicillanic acid or of an ester of a 7-amino-3-cephem-4-carboxylic acid in the presence of the hydrochloride of a weak amine.

4 Claims, No Drawings

P-TRIMETHYLSILYLOXYPHENYL GLYCYLOXYPHTHALIMIDE

BACKGROUND OF THE INVENTION

This invention relates to novel chemical compounds which are useful as intermediates in the synthesis of 6-(p-hydroxyphenylglycylamido)-penam or 7-(p-hydroxyphenylglycylamido)-cephem compounds.

SUMMARY OF THE INVENTION

The novel chemical compounds of the invention have the general formula:

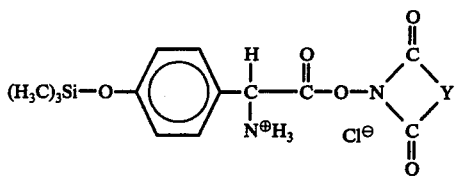

wherein Y is

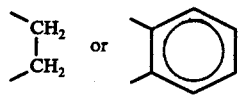

These novel compounds are prepared by reacting D-(−)-p-trimethylsilyloxyphenylglycin-N-carboxyanhydride with a N-hydroxyimide of the general formula:

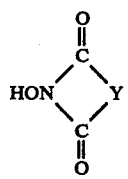

wherein Y has the meaning defined above, in the presence of a hydrochloride of a weak amine and in an inert solvent.

The reaction is preferably carried out in the presence of pyridine hydrochloride and in methylene chloride.

The novel compounds thus prepared may be isolated or may be utilized in situ in a process for the production of 6-(p-hydroxyphenylglycylamido)-penam or 7-(p-hydroxyphenylglycylamido)-cephem compounds as active esters. Several activated esters of protonated amino acids have been described in the literature (Tetrahedron Letters 1965, 95, J. Chem. Soc. C 1968, 1219), but such compounds have only been utilized as amino components in peptide synthesis.

In general, the utilization of proton protection of amino groups in peptide synthesis has up until now met with at least one major obstacle; this being that proton migration is unavoidable, thus hampering the formation of the peptide bond with the unprotonated amino component.

The invention also relates to a process for preparing 6-(p-hydroxyphenylglycylamido)-penam or 7-(p-hydroxyphenylglycylamido)-cephem compounds, the process comprising the steps of reacting a compound of the general formula:

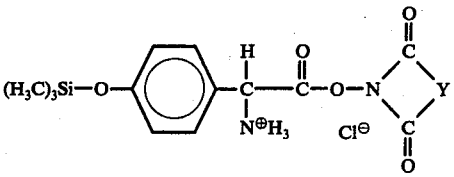

wherein Y is

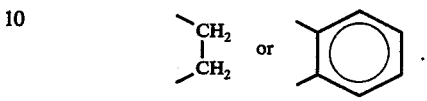

with a phosphite amide of an ester of 6-aminopenicillanic acid or of an ester of 7-amino-3-cephem-4-carboxylic acid in the presence of the hydrochloride of a weak amine.

Phosphite amides of esters of 6-aminopenicillanic acid or of esters of 7-aminocephalosporanic acid are described in Belgian Patent Specification No. 809,110.

Since the acylation of the phosphite amides with the above-defined activated esters is proton catalyzed, a high proton activity has to be maintained in the reaction medium throughout the acylation. Such a high proton activity is preferably provided by using pyridine hydrochloride as the hydrochloride.

The yields obtained by the process of the invention are high and racemisation of the sterically labile D-(−)-p-hydroxyphenylglycyl is not observed.

DESCRIPTION OF THE PREFERRED EMBODIMENTS

EXAMPLE 1 p-Trimethylsilyloxy-D-(−)-phenylglycyloxysuccinimide, hydrochloride 0.575 g (5 mmoles) of N-hydroxysuccinimide was added to a solution of 0.58 g (5 mmoles) of pyridine hydrochloride and 1.33 g (5 mmoles) of p-trimethylsilyloxy-D-(−)-phenylglycine-N-carboxyanhydride in 17 ml of dry methylene chloride at 0° C. Carbon dioxide was evolved, and after 1 hour only traces of N-carboxyanhydride could be detected by a thin layer chromatography (silica gel, benzene/acetone 1:1, sprayed with ninhydrin). The white, crystalline precipitate formed was isolated by filtration to yield 1.02 g (55%) of p-trimethylsilyloxy-D-(−)-phenylglycyloxysuccinimide, hydrochloride. Analysis:

Calculated for $C_{15}H_{21}N_2O_5SiCl$: C: 48.33%, H: 5.68%, N: 7.51%, Cl: 9.51%. Found: C: 48.25%, H: 5.37%, N: 7.54%, Cl: 9.74%.

The IR spectrum (KBr) showed characteristic absorption at 1815 cm$^{-1}$, 1780 cm$^{-1}$ (ester), 1730 cm$^{-1}$, 1710 cm$^{-1}$ (cyclic imide), and 840 cm$^{-1}$ (trimethylsilyl).

The NMR spectrum (D-DMF, Ext.) showed characteristic signals at:

| δ ppm | Correlation | Integral |
| --- | --- | --- |
| 0.05 (s) | Trimethylsilyl | 9 H |
| 2.9 (s) | O=C—CH$_2$—CH$_2$—C=O | 4 H |
| 5.9 (s) | Benzyl-H | 1 H |
| 7.05 (d) J=9 | Aromatic-H | 2 H |
| 7.6 (d) J=9 | Aromatic-H | 2 H |
| 8–10 (broad) | NH | 3 H |

EXAMPLE 2 p-Trimethylsilyloxy-D-(—)-phenylglycyloxyphthalimide, hydrochloride 2.65 g (10 mmoles) of p-trimethylsilyloxy-D-(—)-phenylglycine-N-carboxyanhydride and 1.16 g (10 mmoles) of pyridine hydrochloride were suspended in 200 ml of dry toluene at room temperature. Finely powdered N-hydroxyphthalimide (1.67 g, 10 mmoles) was added, and the mixture was stirred for 24 hours. The precipitate was isolated by filtration and washed thoroughly with methylene chloride to yield 3.66 g (85%) of p-trimethylsilyloxy-D-(—)-phenylglycyloxyphthalimide, hydrochloride.

Analysis: Calculated for $C_{19}H_{21}N_2O_5SiCl$: C: 54.33%; H: 5.03%. Found: C: 54.37%; H: 4.92%.

The IR spectrum (KBr) showed characteristic absorption at 1820 $cm^{-1}$ and 1790 $cm^{-1}$ (ester), 1750 $cm^{-1}$ (cyclic imide), and 840 $cm^{-1}$ (trimethylsilyl).

EXAMPLE 3 p-Hydroxyampicillin.

Method A 4.2 ml (30 mmoles) of triethylamine was added to a suspension of 3.24 g (15 mmoles) of 6-aminopenicillanic acid and the mixture was stirred at room temperature until a clear solution was formed. 1.89 ml (15 mmoles) of trimethylchlorosilane was added dropwise and the mixture stirred for 1 hour, then cooled to 0° C, whereafter 1.35 ml (15 mmoles) of ethylene chlorophosphite was added during ½ hour to produce trimethylsilyl 6-ethylenephosphiteamidopenicillinate. At this point, 2.9 g (25 mmoles) of pyridine hydrochloride, 2.66 g (10 mmoles) of p-trimethylsilyloxy-D-(—)-phenylglycine-N-carboxyanhydride, and 1.15 g (10 mmoles) of N-hydroxysuccinimide were added all at once and in the order mentioned. The mixture was stirred at 0° C overnight, whereafter enzymatic titration indicated a 96% yield of penicillin.

A solution of 6.7 g of sodium dioctyl sulfosuccinate (Manoxol OT, BDH) in 50 ml of ethyl acetate was added, and the methylene chloride evaporated in vacuo. The mixture was poured into ice-water, the pH adjusted to 2 with phosphoric acid, and the phases separated. The aqueous phase was extracted twice with 1.67 g of sodium dioctyl sulfosuccinate in 10 ml of ethyl acetate. The combined organic extracts were added to 10 ml water, and the pH adjusted to 4.9 with dicocomethylamine (KEMAMINE T-6501), and stirred 1 hour at 0° C to complete precipitation of the crystalline p-hydroxyampicillin trihydrate, 3.4 g of the product (80%) was isolated by filtration. Enzymatic titration indicated a purity of 80%, and one reprecipitation from water at iso-electric pH produced the pure compound, showing IR and NMR spectra identical with those of the authentic material.

Method B 2.4 ml (30 mmoles) of pyridine followed by 1.9 ml (15 mmoles) of trimethylchlorosilane and 1.35 ml (15 mmoles) of ethylene chlorophosphite were added to a suspension of 3.24 g (15 mmoles) of 6-aminopenicillanic acid in 23 ml of dry methylene chloride. An exothermic reaction starts, bringing the mixture to a mild reflux. After 2 hours of stirring at room temperature, a small sample was evaporated, dissolved in deuteriochloroform, and the NMR spectrum recorded: (External standard: TMS). The 6-hydrogen was represented by a multiplet of four signals, centered at $\delta = 5$ ppm, from which by first order analysis the following coupling constants were deduced:

| $J_{PNCH}$: 12 Hz | $J_{HCCH}$: 4.5 Hz |
|---|---|

Addition of excess of triethylamine to the NMR tube converted this spectrum to the known pattern of the free base.

The reaction mixture was cooled to 0° C, 2.66 g (10 mmoles) of p-trimethylsilyloxy-D-(—)-phenylglycine-N-carboxyanhydride, and 1.15 g (10 mmoles) of N-hydroxysuccinimide were added, and the mixture stirred at 0° C overnight. Enzymatic titration indicated a yield of 98%. The product was precipitated by addition of 1.6 ml of pyridine and 7 g of activated carbon (NORIT SU 18, containing 7.5% of water). After being stirred for 1 hour at 0° C and 1 hour at room temperature, the precipitate was isolated by filtration and resuspended in 50 ml of icewater. The carbon was removed by filtration (enzymatic titration at this point indicated 75% yield), 4 g sodium perchlorate was added, the pH was adjusted to 1.5 with perchloric acid, and the product extracted with n-butanol as the perchlorate salt. To the combined butanol extracts 50 ml water was added, the pH was adjusted to 7 with triethylamine, and the product extracted back into water. The combined aqueous phases were adjusted to pH 4.8, and dissolved butanol removed by azeotropic distillation in vacuo, whereby the p-hydroxyampicillin crystallized as the trihydrate. The first crop of crystals amounted to 1.66 g (39%), showing IR and NMR spectra identical with those of authentic material. A further crop of crystals were obtained from the filtrate.

EXAMPLE 4 p-Hydroxyampicillin

A suspension of 1.08 g (5 mmoles) of 6-aminopenicillanic acid in 12.5 ml of dry methylene chloride and 1.4 ml (10 mmoles) of triethylamine was stirred at room temperature until a clear solution was obtained. The mixture was then cooled to −40° C, and 0.45 ml (5 mmoles) of ethylene chlorophosphite was added. The mixture was brought to room temperature and stirred for one hour. 0.3 ml (2.5 mmoles) of dimethyldichlorosilane was added and the mixture stirred overnight at 0° C. 0.4 ml of pyridine and 1.86 g (5 mmoles) of p-trimethylsilyloxy-D-(—)-phenylglycyloxysuccinimide, prepared as described in Example 1, were added to the solution.

The reaction was followed by enzymatic titration of penicillin as follows:

| Time | Yield |
|---|---|
| 1½ h | 50% |
| 2½ h | 63% |
| 3½ h | 70% |
| 20 h | 70% |

The penicillin produced behaved identically with authentic p-hydroxyampicillin in high voltage electrophoresis at pH 7. The product was isolated as described in Example 3.

EXAMPLE 5

7-(D-α-amino-α-(p-hydroxyphenyl)-acetamido)-3-(1,2,3-triazol-5-ylthiomethyl)-3-cephem-4-carboxylic acid 1.56 g (5 mmoles) of 7-amino-3-(1,2,3-triazol-5-yl-thiomethyl)-3-cephem-4-carboxylic acid was suspended in 20 ml of dry acetonitrile, 2.1 ml (15 mmoles) of triethylamine was added, and the mixture was stirred for about 2–3 hours at ambient temperature until a clear solution was obtained. The solution was cooled to 0° C, and 0.45 ml (5 mmoles) of ethylenechlorophosphite, dissolved in 2.5 ml of acetonitrile, was added. The mixture was stirred for 30 minutes, brought to room temperature, and 1.26 ml of trimethyl chlorosilane (10 mmoles) was added. After stirring for 2 hours, the precipitated triethylamine hydrochloride was removed by filtration (1.43 g). 2.32 g (20 mmoles) of pyridine hydrochloride, 2.0 g (7.5 mmoles) of p-trimethylsilyloxy-D-(−)-phenylglycine-N-carboxyanhydride and 0.86 g (7.5 mmoles) of N-hydroxysuccinimide was added to the solution of bis-trimethylsilyl-7-ethylenephosphiteamido-3-(1,2,3-triazol-5-yl-thiomethyl)-3-cephem-4-carboxylate, and the mixture was stirred at 0° C overnight. High voltage paper electrophoresis indicated a nearly quantitative acylation.

For recovering of the reaction product, sodium dioctylsulfosuccinate (10 mmoles) was added, the solvent evaporated in vacuo and replaced by 30 ml of ethyl acetate followed by 15 ml of ice-water. The pH was adjusted to 1 and the mixture was stirred for 15 minutes and filtered, followed by separation of the phases. The aqueous phase was extracted twice with 5 ml of ethyl acetate containing sodium dioctylsulfosuccinate (2.5 mmoles).

The transfer of the product to the organic phase was confirmed by paper electrophoresis. The combined organic extracts were treated with 1 g of active carbon (Norit SU 18) and filtered through filter aid. Methanol (9.5 ml) and water (0.5 ml) were added, and pH was adjusted to 4.5 with tricaprylamine. A white precipitate was formed, and after stirring for 1.5 hour at 0° C the product was isolated by filtration, washed with ethyl acetate and methanol and dried in vacuo to yield 1.4 g of a white powder, showing a single spot on high voltage paper electrophoresis, moving as an anion at pH = 8, and as a cation at pH = 5. The NMR spectrum showed signals corresponding to the proposed structure.

I claim:

1. A chemical compound of the formula:

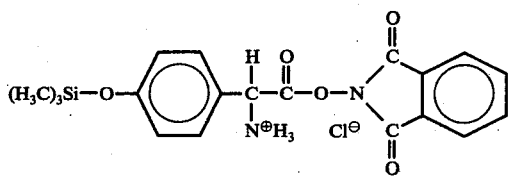

2. A process for preparing a chemical compound of the formula:

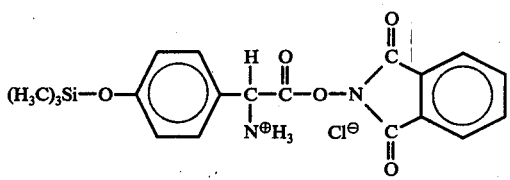

comprising the steps of reacting D-(−)-p-trimethylsilyloxyphenylglycin-N-carboxyanhydride with a N-hydroxyimide of the formula:

in the presence of a hydrochloride of a weak amine and in an inert solvent.

3. A process as claimed in claim 2 wherein the hydrochloride of a weak amine is pyridine hydrochloride.

4. A process as claimed in claim 2 wherein the inert solvent is methylene chloride.

* * * * *

UNITED STATES PATENT OFFICE
CERTIFICATE OF CORRECTION

PATENT NO. : 4,098,796
DATED : July 4, 1978
INVENTOR(S) : Erling Guddal

It is certified that error appears in the above-identified patent and that said Letters Patent are hereby corrected as shown below:

[73]   Assignee: Novo Industri A/S, Bagsvaard, Denmark

[21]   Appl. No.: 693,516

[22]   Filed: Jun. 7, 1976

[30]   Foreign Application Priority Data

June 13, 1975   Great Britain........25447

Signed and Sealed this

Sixth Day of March 1979

[SEAL]

Attest:

RUTH C. MASON
Attesting Officer

DONALD W. BANNER
Commissioner of Patents and Trademarks